US011215613B2

(12) United States Patent
Nagae et al.

(10) Patent No.: US 11,215,613 B2
(45) Date of Patent: Jan. 4, 2022

(54) DETECTION DEVICE, DETECTION METHOD USING SAID DETECTION DEVICE, AND DETECTION CHIP USED IN SAID DETECTION DEVICE

(71) Applicant: KONICA MINOLTA, INC., Chiyoda-ku (JP)

(72) Inventors: Kosuke Nagae, Chiyoda-ku (JP); Hiroshi Hirayama, Chiyoda-ku (JP)

(73) Assignee: KONICA MINOLTA, INC., Tokyo (JP)

( * ) Notice: Subject to any disclaimer, the term of this patent is extended or adjusted under 35 U.S.C. 154(b) by 522 days.

(21) Appl. No.: 15/033,319

(22) PCT Filed: Oct. 31, 2014

(86) PCT No.: PCT/JP2014/079125
§ 371 (c)(1),
(2) Date: Apr. 29, 2016

(87) PCT Pub. No.: WO2015/064757
PCT Pub. Date: May 7, 2015

(65) Prior Publication Data
US 2016/0266111 A1 Sep. 15, 2016

(30) Foreign Application Priority Data
Oct. 31, 2013 (JP) .............................. JP2013-226952

(51) Int. Cl.
*G01N 33/553* (2006.01)
*G01N 33/543* (2006.01)
(Continued)

(52) U.S. Cl.
CPC ...... *G01N 33/54373* (2013.01); *B01L 3/5027* (2013.01); *G01N 1/14* (2013.01);
(Continued)

(58) Field of Classification Search
CPC .......... G01N 33/54373; G01N 21/553; G01N 21/0332; G01N 1/14; G01N 21/6428;
(Continued)

(56) References Cited

U.S. PATENT DOCUMENTS 6,326,612 B1 12/2001 Elkind et al.
2007/0209533 A1* 9/2007 Suda ...................... C23C 14/14
100/318

(Continued)

FOREIGN PATENT DOCUMENTS

EP 2693217 2/2014
JP 6-167443 6/1994
(Continued)

OTHER PUBLICATIONS

Search Report dated May 11, 2017 which issued in the corresponding European Patent Application No. 14856943.7.
(Continued)

*Primary Examiner* — Christopher L Chin
(74) *Attorney, Agent, or Firm* — Cozen O'Connor

(57) ABSTRACT

This detection device has a holder and a heating unit. The holder holds a detection chip that has the following: a prism that has an incidence surface and a film-formation surface; a metal film formed on said film-formation surface; trapping bodies laid out on the surface of said metal film; and a substrate that is laid out on the surface of the metal film, and together with the metal film, forms a liquid collection section in which a liquid is collected. The heating unit heats at least one of the substrate, the prism, and the metal film either while in contact therewith or without contacting same. Also, the heating unit is positioned so as to avoid the path that excitation light takes from an excitation-light emission unit to the abovementioned incidence surface.

8 Claims, 10 Drawing Sheets

(51) Int. Cl.
*G01N 21/64* (2006.01)
*G01N 21/552* (2014.01)
*G01N 21/03* (2006.01)
*B01L 3/00* (2006.01)
*G01N 1/14* (2006.01)
*G01N 21/13* (2006.01)

(52) U.S. Cl.
CPC ....... *G01N 21/0332* (2013.01); *G01N 21/553* (2013.01); *G01N 21/648* (2013.01); *G01N 21/6428* (2013.01); *G01N 33/553* (2013.01); *B01L 2200/16* (2013.01); *B01L 2300/0636* (2013.01); *B01L 2300/0654* (2013.01); *B01L 2300/1816* (2013.01); *G01N 21/13* (2013.01); *G01N 2021/6439* (2013.01); *G01N 2201/0231* (2013.01); *G01N 2201/064* (2013.01); *G01N 2201/06113* (2013.01)

(58) Field of Classification Search
CPC .... G01N 33/553; G01N 21/648; G01N 21/13; G01N 2021/6439; G01N 2201/0231; G01N 2201/06113; G01N 2201/064; B01L 3/5027; B01L 2300/1816; B01L 2300/0636; B01L 2200/16; B01L 2300/0654
USPC ............. 422/82.11; 435/288.7, 808; 436/805
See application file for complete search history.

(56) References Cited

U.S. PATENT DOCUMENTS

| | | | | |
|---|---|---|---|---|
| 2007/0298433 | A1* | 12/2007 | Sia | G01N 33/543 435/7.1 |
| 2009/0075390 | A1* | 3/2009 | Linder | B01L 3/502715 436/161 |
| 2009/0218496 | A1* | 9/2009 | Kimura | G01N 21/553 250/362 |
| 2010/0167318 | A1* | 7/2010 | Linder | B01L 3/502746 435/7.92 |
| 2014/0030151 | A1* | 1/2014 | Horii | G06F 1/206 422/69 |
| 2015/0188007 | A1* | 7/2015 | Mochizuki | H01L 33/56 257/98 |

FOREIGN PATENT DOCUMENTS

| | | | | |
|---|---|---|---|---|
| JP | H 10307141 | 11/1998 | | |
| JP | 2000-65732 | 3/2000 | | |
| JP | 2001-108619 | 4/2001 | | |
| JP | 2003-98074 | 4/2003 | | |
| JP | 2004 286599 | 10/2004 | | |
| JP | 2009-532031 | 9/2009 | | |
| JP | 2009-264744 | 11/2009 | | |
| JP | 2009-270931 | 11/2009 | | |
| JP | 2012-122977 | 6/2012 | | |
| JP | 2012-215465 | 8/2012 | | |
| WO | WO-2008034896 | A2 * | 3/2008 | ........ B01L 3/502715 |
| WO | WO 2010/010858 | | 1/2010 | |
| WO | WO2012/042805 | | 4/2012 | |
| WO | WO 2012/108323 | | 8/2012 | |
| WO | WO-2012132451 | A1 * | 10/2012 | ............. G06F 1/206 |
| WO | WO-2013180259 | A1 * | 12/2013 | ............. H01L 33/56 |

OTHER PUBLICATIONS

Office Action dated May 8, 2018 which issued in the corresponding Japanese Patent Application No. 2015-545333.

* cited by examiner

DETECTION DEVICE, DETECTION METHOD USING SAID DETECTION DEVICE, AND DETECTION CHIP USED IN SAID DETECTION DEVICE

RELATED APPLICATIONS

This is a U.S. National Phase Application under 35 USC 371 of International Application PCT/JP2014/079125 filed on Oct. 31, 2014.

This application claims the priority of Japanese application no. 2013-226952 filed Oct. 31, 2013, the entire content of which is hereby incorporated by reference.

TECHNICAL FIELD

The present invention relates to a detection device that detects a detection target substance using surface plasmon resonance, and also relates to a detection method using the detection device and to a detection chip used in the detection device.

BACKGROUND ART

Highly-sensitive and quantitative detection of a minute amount of a detection target substance such as protein and/or DNA in laboratory tests or the like makes it possible to perform treatment while quickly determining the patient's condition. For this reason, the analysis device and the analysis method which can highly-sensitively and quantitatively detect a minute amount of a detection target substance have been in demand.

Surface plasmon-field enhanced fluorescence spectroscopy (hereinafter abbreviated as "SPFS") is known as a method which can detect a detection target substance with high sensitivity (see, for example, PTLs 1 and 2).

PTLs 1 and 2 disclose an analysis device and an analysis method that utilize SPFS. In the analysis device and analysis method, a sensor chip including: a prism composed of dielectric; a metal film formed on one surface of the prism; and a capturing body (e.g., antibody) fixed onto the metal film, is used. When a sample containing a detection target substance is provided on the metal film, the detection target substance is captured by the capturing body (primary reaction). The captured detection target substance is further labeled by a fluorescent material (secondary reaction). In this state, when the metal film is irradiated with excitation light through the prism at an angle at which surface plasmon resonance occurs, localized-field light can be generated on the surface of the metal film. With this localized-field light, the fluorescent material used for labeling the captured detection target substance on the metal film is selectively excited, and the fluorescence emitted from the fluorescent material is observed. In the analysis device and analysis method, the fluorescence is detected to detect the presence or amount of the detection target substance. Normally, the analysis method using the analysis device is performed at room temperature.

CITATION LIST

Patent Literature

PTL 1
Japanese Patent Application Laid-Open No. HEI 10-307141
PTL 2
WO 2012-042805

SUMMARY OF INVENTION

Technical Problem

In general, the primary reaction and the secondary reaction vary depending on the surrounding temperature. When an antibody is used, the primary reaction and the secondary reaction are most promoted at around 37 degrees, which is higher than room temperature. Moreover, the intensity of fluorescence emitted from the fluorescent material also varies depending on the surrounding temperature.

In the analysis device and analysis method disclosed in PTLs 1 and 2, however, the temperature of the reaction site is not managed, so that the temperatures of the reaction sites at the time of the primary reaction, the secondary reaction and the fluorescent detection have to be dependent on the installation environment of the analysis device. Accordingly, the analysis device and analysis method disclosed in PTLs 1 and 2 involve concern that there may be a change, depending on the surrounding temperature, in the rate of a detection target substance being captured by the capturing body in the primary reaction, the rate of a detection target substance being labeled by fluorescence in the secondary reaction, and the intensity of fluorescence at the time of fluorescent detection. Accordingly, there is concern that the analysis device and analysis method disclosed in PTLs 1 and 2 cannot detect a detection target substance contained in a sample, highly-sensitively and quantitatively.

An object of the present invention is to provide a detection device capable of highly-sensitively and quantitatively detecting a detection target substance, using surface plasmon resonance. Still, another object of the present invention is to provide a detection method using this detection device. Yet, another object of the present invention is to provide a detection chip used in this detection device.

Solution to Problem

To solve the above-mentioned problems, the detection device according to an embodiment of the present invention is a detection device that detects the presence or amount of a detection target substance contained in a sample, using surface plasmon resonance, the detection device including: a holder that holds a detection chip, the detection chip including: a prism including an incident surface and a film formation surface, a metal film disposed on the film formation surface; a capturing body disposed on the metal film; and a base body disposed to be flush with a surface of the metal film, the surface being where the capturing body is disposed, and the base body being configured to form, together with the metal film, a liquid reservoir section that reserves a liquid, an excitation light irradiation section that emits excitation light toward the incident surface; and a heating section that heats at least any one of the base body, the prism, and the metal film, in a contact state or a non-contact state, in which the heating section is disposed while avoiding a light path of the excitation light from the excitation light irradiation section to the incident surface.

In addition, to solve the above-mentioned problems, the detection method according to an embodiment of the present invention is a detection method for detecting the presence or amount of a detection target substance contained in a sample, using surface plasmon resonance, the method including: preparing a detection chip comprising a detection section, the detection section including a prism including an incident surface and a film formation surface, a metal film disposed on the film formation surface, a capturing body fixed onto the metal film, and a base body disposed to be flush with a surface of the metal film, the surface being where the capturing body is disposed, and the base body being configured to form, together with the metal film, a liquid reservoir section that reserves the sample; heating at least any one of the base body, the prism, and the metal film of the detection chip; bonding a detection target substance contained in the sample to the capturing body by causing the sample to be in contact with the capturing body; and emitting excitation light to the metal film from a direction of the prism such that the excitation light is totally reflected at a surface boundary between the prism and the metal film.

Moreover, to solve the above-mentioned problems, the detection chip according to an embodiment of the present invention is a detection chip used in a detection device that detects the presence or amount of a detection target substance contained in a sample, using surface plasmon resonance, the detection chip including: a prism including an incident surface and a film formation surface; a metal film disposed so as to extend to an outer side of the film formation surface; a capturing body disposed on the metal film; and a base body disposed to be flush with a surface of the metal film, the surface being where the capturing body is disposed, and the base body being configured to form, together with the metal film, a liquid reservoir section that reserves a liquid.

Advantageous Effects of Invention

According to the present invention, the temperature at the reaction site can be constant every time, so that a detection target substance can be highly-sensitively and quantitatively detected.

DESCRIPTION OF EMBODIMENTS

In the following, an embodiment of the present invention is described in detail with reference to the accompanying drawings.

Embodiment 1

In Embodiment 1, a description will be given of an embodiment of an SPFS device which is a detection device according to the present invention.

First, an outline of the SPFS device will be described. The SPFS device generates localized-field light (which is called "evanescent light" or "near-field light" in general) on a surface of a metal film by causing excitation light to enter the metal film on a prism composed of dielectric, at an angle at which surface plasmon resonance occurs. The SPFS device detects the presence or amount of a detection target substance by detecting, when a fluorescent material used to label a detection target substance disposed on the metal film is selectively excited by this localized-field light, the light amount of the fluorescence emitted from the fluorescent material.

Figure 1:
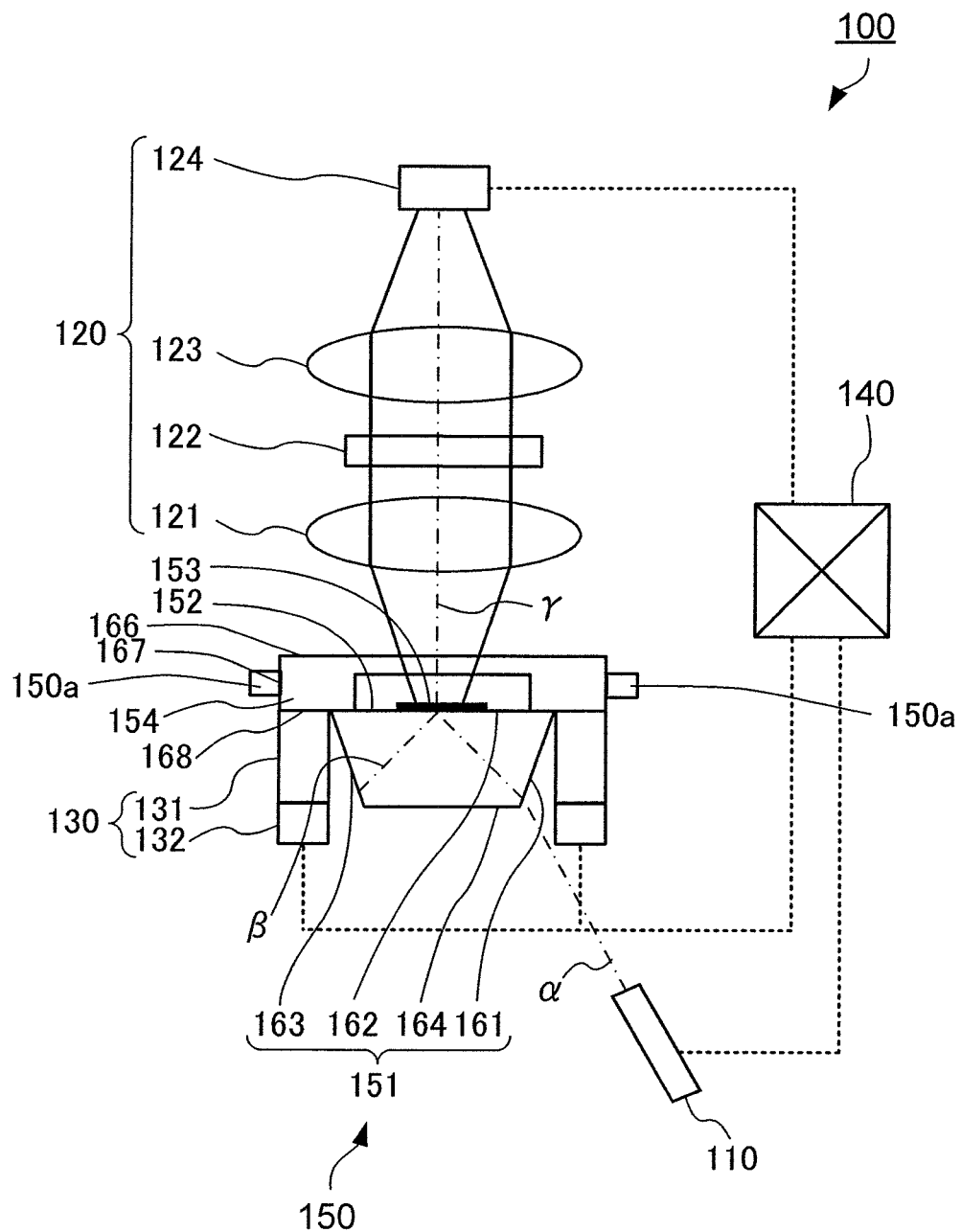
FIG. 1 is a schematic view of an SPFS device according to Embodiment 1.

FIG. 1 is a schematic diagram illustrating a configuration of SPFS device 100 according to Embodiment 1. As illustrated in FIG. 1, SPFS device 100 includes excitation light irradiation section 110, light detection section 120, heating section 130, and control section 140. In detection of a detection target substance, SPFS device 100 is used in a state where detection chip 150 is attached to holder 150a. For this reason, detection chip 150 will be described, first, and each configuration element of SPFS device 100 will be described, thereafter.

Figure 2A:
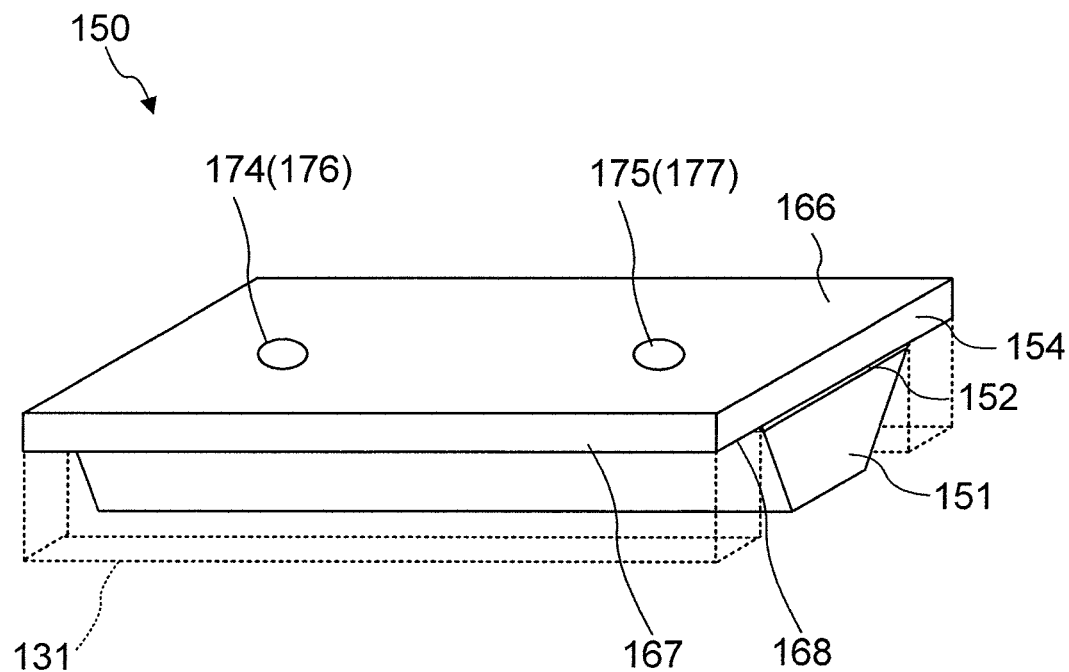
FIGS. 2A and 2B are diagrams illustrating a configuration of a detection chip according to Embodiment 1.
Figure 2B:
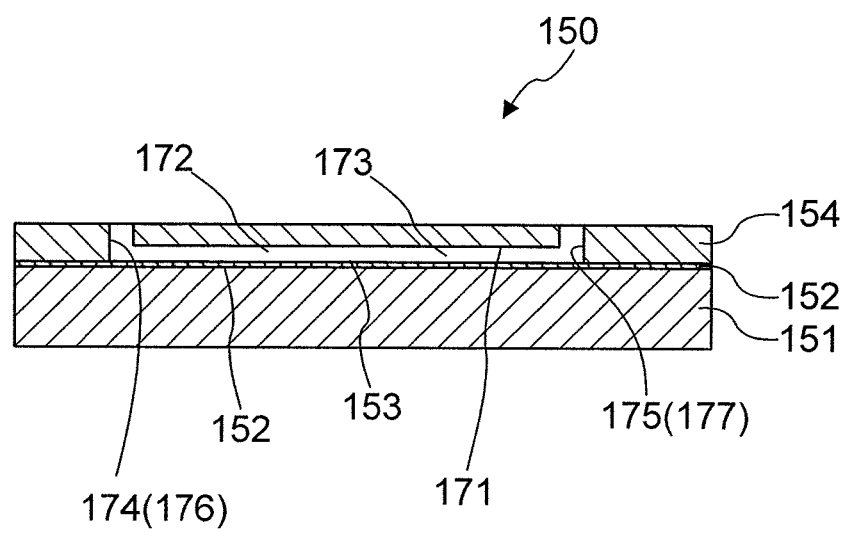

FIGS. 2A and 2B are diagrams illustrating a configuration of detection chip 150. FIG. 2A is a perspective view of detection chip 150, and FIG. 2B is a cross-sectional view taken along a long-side direction of detection chip 150. Note that, FIG. 2A illustrates, using a broken line, heat block 131 to be described hereinafter. As illustrated in FIG. 1 and FIGS. 2A and 2B, detection chip 150 includes prism 151, metal film 152, reaction section 153, and base body 154. Normally, detection chip 150 is replaced every detection. The size of detection chip 150 is not limited in particular, and the length of each side of detection chip 150 is preferably about several millimeters to several centimeters.

Prism 151 is composed of dielectric which is transparent with respect to excitation light α. Prism 151 includes incidence surface 161, film formation surface (reflection surface) 162, emission surface 163, and bottom surface 164. Incidence surface 161 is a surface through which excitation light α emitted from excitation light irradiation section 110 enters prism 151. Film formation surface 162 reflects excitation light α that has entered prism 151. Excitation light γ that has been reflected by film formation surface 162 becomes reflection light β. As will be described hereinafter, metal film 152 is disposed on film formation surface 162. Emission surface 163 causes reflection light β to be emitted out of prism 151. Bottom surface 164 is disposed to be opposite to film formation surface 162.

The shape of prism 151 is not limited in particular. In the present embodiment, the shape of prism 151 is a column having a trapezoidal bottom surface. In this case, the surface corresponding to a bottom side of the trapezoid is film formation surface 162 and the surface corresponding to the other bottom side of the trapezoid is bottom surface 164, the surface corresponding to one of the legs is incidence surface 161, and the surface corresponding to the other leg is emission surface 163. Examples of the material of prism 151 include a resin and glass. Preferably, the material of prism 151 is a resin having a refractive index within a range from 1.4 to 1.6 and exhibiting a small birefringence.

Metal film 152 is disposed on film formation surface 162 of prism 151. Thus, the interaction (surface plasmon resonance) occurs between the photons of excitation light α which has entered film formation surface 162 under the total reflection condition and the free electrons in metal film 152, and thus localized-field light can be generated on the surface of metal film 152.

The material of metal film 152 is not limited in particular as long as the material is a metal that causes surface plasmon resonance. Examples of the material of metal film 152 include gold, silver, copper, aluminum, and their alloys. In the present embodiment, metal film 152 is a metal film. The formation method for metal film 152 is not limited in particular. Examples of the formation method for metal film 152 include sputtering, deposition, and plating. Preferably, the thickness of metal film 152 is within a range from 30 nm to 70 nm, but is not limited in particular.

Reaction section 153 is disposed on a surface of metal film 152 where prism 151 is not disposed (top surface) among two surfaces (top surface and rear surface) of metal film 152. Reaction section 153 contains a primary antibody (capturing body) for capturing a detection target substance and captures the detection target substance. The detection target substance captured by the primary antibody is labeled with fluorescence by a secondary antibody labeled by a fluorescent material. In such a situation, reaction section 153 excites the fluorescent material by localized-field light generated by irradiating metal film 152 with excitation light α, and fluorescence γ is emitted.

Base body 154 is disposed on the surface of metal film 152 where prism 151 is not disposed (top surface). Base body 154 includes top surface 166, side surface 167, and bottom surface 168. In this embodiment, base body 154 is disposed so as to cover reaction section 153 and is a substantially plate-shaped transparent member formed to have a size greater than film formation surface 162 of prism 151. Channel groove 171 is formed in the surface of base body 154 that faces metal film 152 (bottom surface 168). Base body 154 is joined to metal film 152 or prism 151 by bonding using an adhesive or by laser welding, ultrasound welding, or pressure bonding using a clamp member, or the like, for example. In this embodiment, base body 154 forms, together with metal film 152, channel 172 having liquid reservoir section 173, by being bonded to metal film 152.

In addition to channel groove 171, base body 154 includes first through hole 174 formed at one end of channel groove 171 and second through hole 175 formed at another end of channel groove 171. First and second through holes 174 and 175 each have a cylindrical shape. Channel groove 171 becomes channel 172 when an opening section of channel groove 171 is closed by metal film 152. In addition, when the opening section of channel 172 is closed by metal film 152, first and second through holes 174 and 175 become injection port 176 and extraction port 177 to and from channel 172, respectively. A liquid-feeding section (illustration is omitted) can be connected to injection port 176.

The sample is not limited to a particular kind. Examples of the sample include blood or serum, plasma, urine, nasal fluid, saliva, feces, coelomic fluid (spinal fluid, ascetic fluid, pleural effusion), and a diluted solution thereof. In addition, examples of the detection target substance contained in the sample include nucleic acid (single-stranded or double-stranded DNA, RNA, polynucleotide, oligonucleotide, peptide nucleic acid (PNA), nucleoside, nucleotide, or a modifier thereof), protein (polypeptide or oligopeptide), amino acid (including modified amino acid), carbohydrate (oligosaccharide, polysaccharide, or sugar chain), fat, or a modifier thereof, and a complex thereof or the like. More specifically, the detection target substance is carcinoembryonic antigen such as α fetoprotein (AFP), tumor marker, signal transducer, or hormone, or the like.

The material of base body 154 is required to be well-formable (transferable, separable), highly-transparent, low in auto-fluorescence with respect to ultraviolet rays and visible light, and high in thermal conductivity, for example. For this reason, the material of base body 154 is favorably a transparent resin. Examples of the resin to be used as the material of base body 154 include polycarbonate, polymethylmethacrylate, polystyrene, polyacrylonitrile, polyvinyl chloride, polyethylene terephthalate, nylon 6, nylon 66, polyvinyl acetate, polyvinylidene chloride, polypropylene, polyisoprene, polyethylene, polydimethylsiloxane, and cyclic polyolefin. In terms of high refractive index, polycarbonate is favorable. The manufacturing method for base body 154 is not limited in particular, but injection molding using a mold is favorable in terms of manufacturing cost.

As illustrated in FIG. 1, excitation light α enters prism 151 from incidence surface 161. Excitation light α having entered prism 151 is incident on metal film 152 at a total reflection angle (an angle at which surface plasmon resonance is caused). Metal film 152 is irradiated with excitation light α at an angle which causes surface plasmon resonance in the above-mentioned manner, and thus it is possible to generate localized-field light on metal film 152. With the localized-field light, the fluorescent material used for labeling the detection target substance on metal film 152 is excited, and fluorescence γ is emitted. By detecting the light amount of fluorescence γ emitted from the fluorescent material, SPFS device 100 detects the presence or amount of the detection target substance.

Next, the configuration elements of SPFS device 100 are described. As described above, SPFS device 100 includes excitation light irradiation section 110, light detection section 120, heating section 130, and control section 140. Although no illustration is given in particular, SPFS device 100 may be covered by a transparent case.

Excitation light irradiation section 110 emits excitation light α to metal film 152 of detection chip 150. Excitation light α is totally reflected by metal film 152 and becomes reflection light β. Excitation light irradiation section 110 has a light source. The light source is turnable around a predetermined point in detection chip 150 and is capable of changing the incident angle of excitation light α with respect to metal film 152. The light source is not limited to a particular type. Examples of the light source include a gas laser, solid-state laser, and semiconductor laser. For example, excitation light α is gas-laser light or solid-state laser light having a wavelength of 200 nm to 1000 nm or semiconductor laser light having a wavelength of 385 nm to 800 nm.

Light detection section 120 detects fluorescence γ emitted from metal film 152. Light detection section 120 is disposed so as to face a surface of metal film 152 of detection chip 150 held by holder 150a, and this surface of metal film 152 is the surface not facing prism 151. Light detection section 120 includes first lens 121, filter 122, second lens 123, and light sensor 124.

First lens 121 and second lens 123 form a conjugate light system which is less likely to be influenced by stray light. The light proceeds between first lens 121 and second lens 123 becomes substantially parallel light. First lens 121 and second lens 123 form an image of fluorescence γ emitted from metal film 152 on a light reception surface of light sensor 124.

Filter 122 is disposed between first lens 121 and second lens 123. Filter 122 contributes to improving the accuracy and sensitivity of fluorescence detection by light sensor 124. Filter 122 is, for example, an optical filter or cut filter. Examples of the optical filter include a neutral density (ND) filter and a diaphragm lens or the like. The cut filter removes outside light (illumination light other than the device), a transparent component of excitation light α, stray light (scattering component of excitation light α), plasmon scattering light (scattering light originated from excitation light α and generated due to the influence of an attachment on the surface of detection chip 150), and a noise component such as auto-fluorescence of each member. Examples of the cut filter include an interference filter and a color filter or the like.

Light sensor 124 detects fluorescence γ emitted from detection chip 150 and passed through filter 122. Examples of light sensor 124 include an ultrasensitive photomultiplier tube, and a CCD image sensor capable of multipoint measurement or the like.

Heating section 130 indirectly heats a liquid at the reaction site, which has been reserved in liquid reservoir section 173, via base body 154. Heating section 130 includes heat block 131 and heat source 132. Heat block 131 heats the liquid at the reaction site in a contact state or non-contact state with base body 154 or to a temperature at the time of analysis. In this embodiment, heat block 131 is a cuboid shape and in contact with base body 154 at least during heating. More specifically, heat block 131 is in contact with bottom surface 168 of base body 154 while avoiding prism 151, and is disposed at both end portions of channel 172 in the width direction of channel 172 (see FIG. 2A). In addition, heat block 131 is disposed while avoiding a light path of excitation light α emitted from excitation light irradiation section 110. Note that, SPFS device 100 may be configured to monitor the temperature of the liquid at the reaction site using a temperature sensor.

The material of heat block 131 is not limited in particular as long as the material allows heat block 131 to heat base body 154, but a metal having a good heat conductivity may be favorably used, for example. The material of heat block 131 is copper or aluminum, for example. The number of and size of heat blocks 131 are not limited in particular and may be appropriately set in accordance with the amount of liquid at the reaction site to be heated.

Accordingly, heat block 131 does not interfere with the functions of SPFS device 100. Moreover, a design taking into account the usability (avoiding burn injury and/or attachment and removal of detection chip 150) can be simply implemented as compared with the case where another surface of base member 154 is heated (see FIG. 4A). In addition, since heat block 131 does not approach the reaction site, a detection error due to a temperature change unlikely occurs. Furthermore, since heat block 131 and prism 151 are not brought into contact with each other, generation of internal stress of prism 151, i.e., of birefringence is suppressed to keep a good excitation light polarization state.

Heat source 132 is connected to control section 140 and heats heat block 131. As with heat block 131, heat source 132 is disposed while avoiding the light path of excitation light α emitted from excitation light irradiation section 110. More specifically, heat section 130 is disposed while avoiding the light path of excitation light α emitted from excitation light irradiation section 110. Heat source 132 is by no means limited to a particular kind, and includes a cartridge heater, rubber heater, infrared heater such as a ceramic heater and a Peltier device or the like. The temperature of heat source 132 is not limited to a particular temperature as long as the temperature allows the liquid at the reaction site in liquid reservoir section 173 to be heated to a temperature of 34 degrees to 40 degrees (temperature at the time of analysis). In Embodiment 1, the temperature of heat source 132 is 40 degrees to 50 degrees.

Heat block 131 heated by heat source 132 heats base body 154. In addition, the heat conducted from the contact position with heat block 131 (bottom surface 168 of base body 154) is conducted to the entirety of base body 154. At this time, the heat conducted to base body 154 is conducted to the liquid of liquid reservoir section 173 of channel 172. Thus, the liquid at the reaction site in liquid reservoir section 173 is heated to the temperature at the time of analysis by heating section 130.

Control section 140 comprehensively controls excitation light irradiation section 110, light detection section 120, and heating section 130. Control section 140 includes, for example, a known computer or a microcomputer or the like having an arithmetic device, a controller, a storage, an input unit and an output unit.

Figure 3:
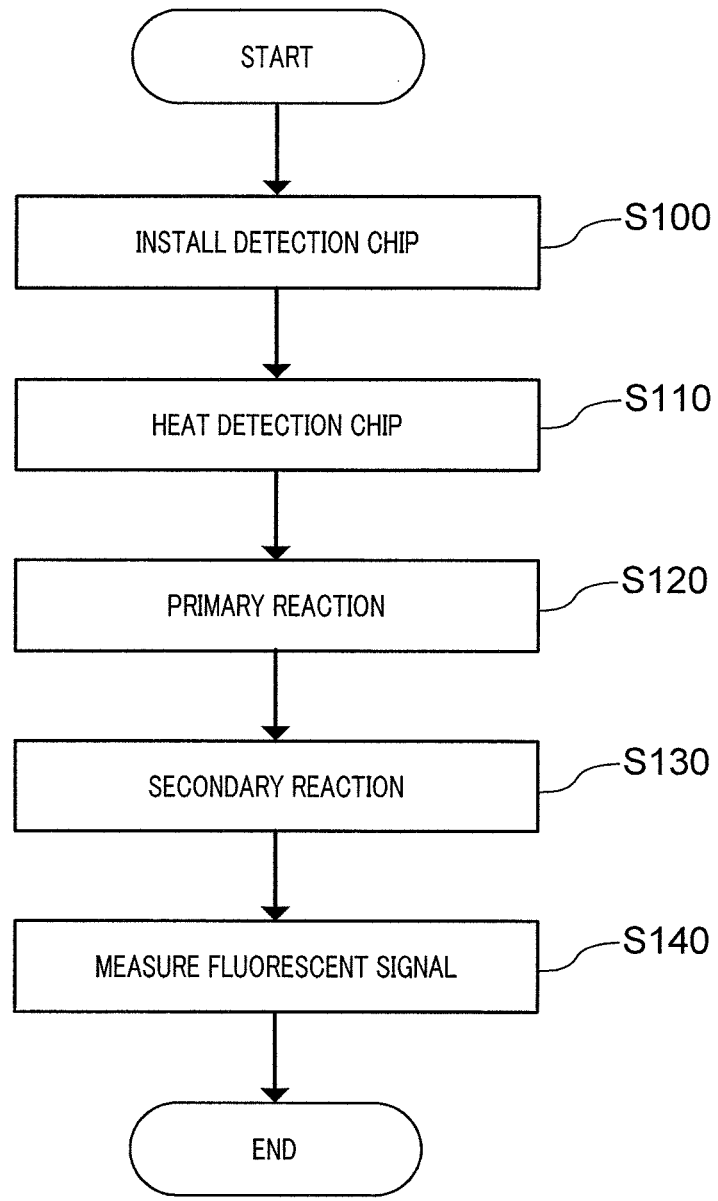
FIG. 3 is a flowchart of an operation procedure of the SPFS device according to Embodiment 1.

Next, a detection operation of SPFS device 100 (detection method according to Embodiment 1 of the present invention) will be described. FIG. 3 is a flowchart illustrating an example of an operation procedure of SPFS device 100.

First, detection chip 150 is installed in holder 150a of SPFS device 100 (S100). At this time, detection chip 150 is installed such that heat block 131 of heating section 130 is in contact with bottom surface 168.

Next, control section 140 operates heat source 132 and heats heat block 131 (S110). Thus, the liquid at the reaction site in liquid reservoir section 173 is heated to a temperature at the time of analysis. In Embodiment 1, the temperature of the liquid at the reaction site at the time of analysis is 37 degrees and is an optimum temperature for the primary reaction and the secondary reaction.

Next, a sample that may contain a detection target substance is fed through channel 172 (S120). In channel 172, a pump is driven to reciprocate the sample in channel 172 in order for a capturing body (primary antibody) fixed to reaction section 153 to surely capture the detection target substance (in order to cause antigen-antibody reaction). At this time, since the inside of liquid reservoir section 173 is adjusted to the same temperature as the temperature at the time of analysis, the sample fed through channel 172 (liquid reservoir section 173) is heated to the temperature at the time of analysis immediately after being fed. The detection target substance contained in the sample is surely captured by the capturing body (primary antibody). Subsequently, the sample in channel 172 is removed, and the inside of channel 172 is cleaned using a cleaning liquid.

Subsequently, a reagent containing the secondary antibody labeled by a fluorescent material is fed through channel 172 via a pump (S130). In this case as well, the reagent fed through channel 172 is heated to the temperature at the time of analysis immediately after being fed. The secondary antibody labeled by a fluorescent material contained in the reagent is surely bonded to the detection target substance. Note that, a sample and reagent may be previously mixed together, and the liquid is fed through a channel in a state where the detection target substance and the secondary antibody are previously bonded to each other. Accordingly, the detection target substance is labeled by a fluorescent material. Subsequently, the reagent (labeling solution) in channel 172 is removed, and the inside of channel 172 is cleaned using a cleaning liquid.

Subsequently, detection chip 150 is irradiated with excitation light α from the light source in order for excitation light α to be incident on metal film 152 at a specific incident angle (see FIG. 1) (S140). With this localized-field light, the fluorescent material used for labeling the detection target substance captured on reaction section 153 is efficiently excited, and fluorescence γ is emitted.

The presence or amount of the detection target substance of the sample can be detected by the above procedure.

(Variations)

An SPFS device according to a variation of Embodiment 1 is different from SPFS device 100 according to Embodiment 1 in the configuration of the heat block. In this respect, the portion different from SPFS device 100 according to Embodiment 1 will be mainly described.

Figure 4A:
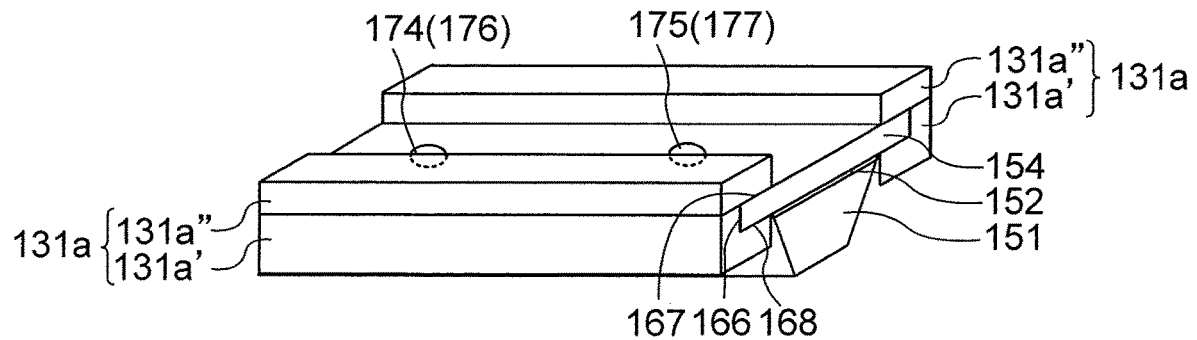
FIGS. 4A to 4C are diagrams illustrating a positional relationship between the detection chip according to Embodiment 1 and a heat block of a variation.
Figure 4B:
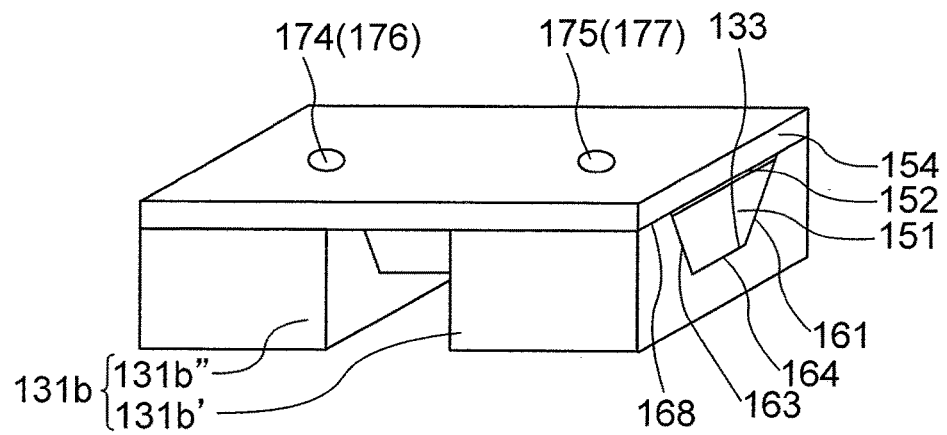
Figure 4C:
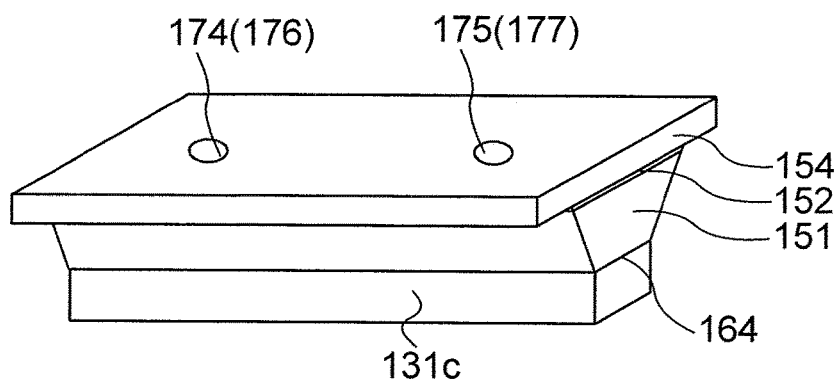

FIGS. 4A to 4C are diagrams illustrating a positional relationship between detection chip 150 and the heat block of the variations. FIG. 4A is a diagram illustrating the positional relationship between detection chip 150 and heat block 131a of Variation 1, FIG. 4B is a diagram illustrating the positional relationship between detection chip 150 and heat block 131b of Variation 2, and FIG. 4C is a diagram illustrating the positional relationship between detection chip 150 and heat block 131c of Variation 3.

As illustrated in FIG. 4A, heat block 131a may be configured to heat base body 154 from top surface 166, side surface 167, and bottom surface 168. In this case, heat block 131a is divided into bottom-side heat block piece 131a' and top-side heat block piece 131a". Bottom-side heat block piece 131a' heats base body 154 from bottom surface 168 and side surface 167. Top-side heat block piece 131a" heats base body 154 from top surface 166. At this time, bottom-side heat block piece 131a' and top-side heat block piece 131a" heat base body 154 while holding base body 154 in between with pressure. Accordingly, detection chip 150 can be effectively heated as compared with heat block 131 according to Embodiment 1. Note that, although no illustration is given in particular, heat block 131 may be configured to heat base body 154 while pushing base body 154 only from side surface 167, or may be configured to heat base body 154 while pushing base body 154 only from top surface 166. When configured to heat base body 154 while pushing base body 154 only from top surface 166, heat block 131 is disposed so as to avoid the fluorescent light path.

As illustrated in FIG. 4B, heat block 131b may be configured to perform heating from the bottom side of detection chip 150. In this case, recess portion 133 is formed in heat block 131b, which is in contact with bottom surface 168 of base body 154, bottom surface 164 of prism 151, incident surface 161 of prism 151, and emission surface 163 of prism 151. Heat block 131b includes first heat block 131b' on the side of extraction port 177 and second heat block 131b" on the side of injection port 176. In this variation, first heat block 131b' and second heat block 131b" are formed in an identical shape and disposed so as to avoid the light path of excitation light α from excitation light irradiation section 110 to incident surface 161. Moreover, as illustrated in FIG. 4C, heat block 131c may be configured to heat bottom surface 164 of prism 151. In this case, a design taking into account the usability (avoiding burn injury or the like and/or attachment and removal of detection chip 150) can be simply implemented as compared with heat block 131a indicated in FIG. 4A. Thus, detection chip 150 can be effectively heated as compared with heat block 131 according to Embodiment 1. In addition, the temperature difference among points in prism 151 is made small, so that it is made easier to avoid deformation of prism 151 caused by thermal stress and also to avoid a change in optical characteristics.

(Variation of Detection Chip)

Detection chips 150' and 150" according to the variations used in SPFS device 100 of Embodiment 1 are different from detection chip 150 according to Embodiment 1 in size or the like of metal film 152'. Thus, the portion different from detection chip 150 according to Embodiment 1 will be mainly described.

Figure 5A:
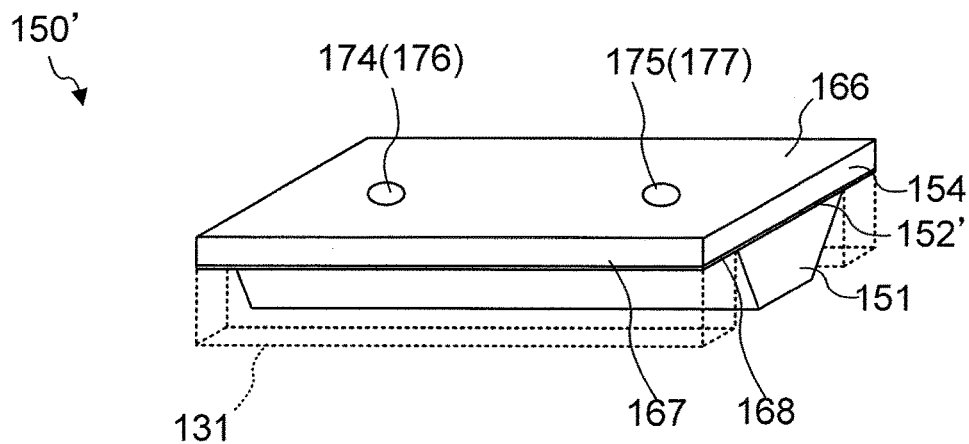
FIGS. 5A to 5C are diagrams illustrating a positional relationship between a detection chip according to Variation 1 of Embodiment 1 and each heat block.
Figure 5B:
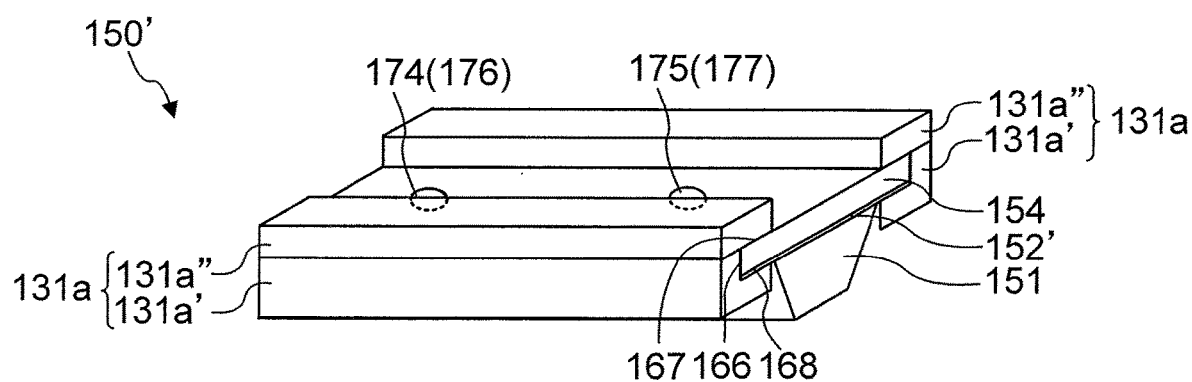
Figure 5C:
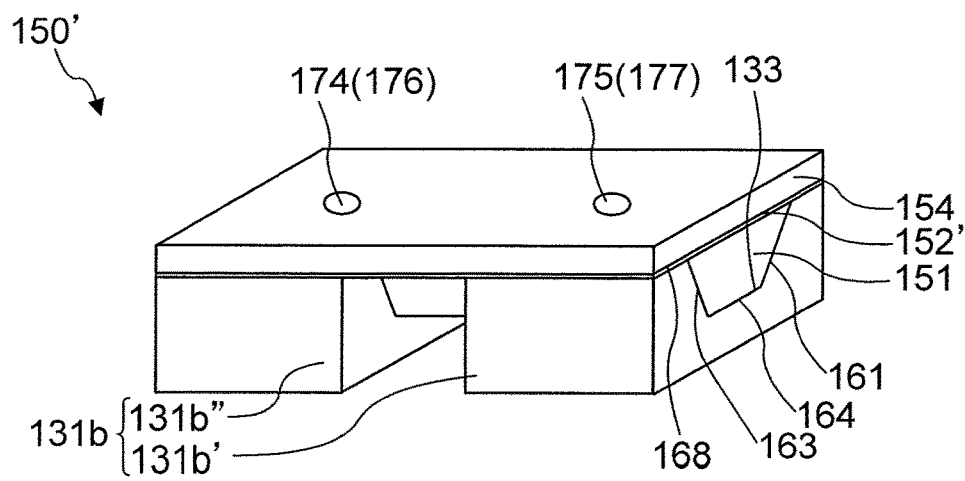
Figure 6:
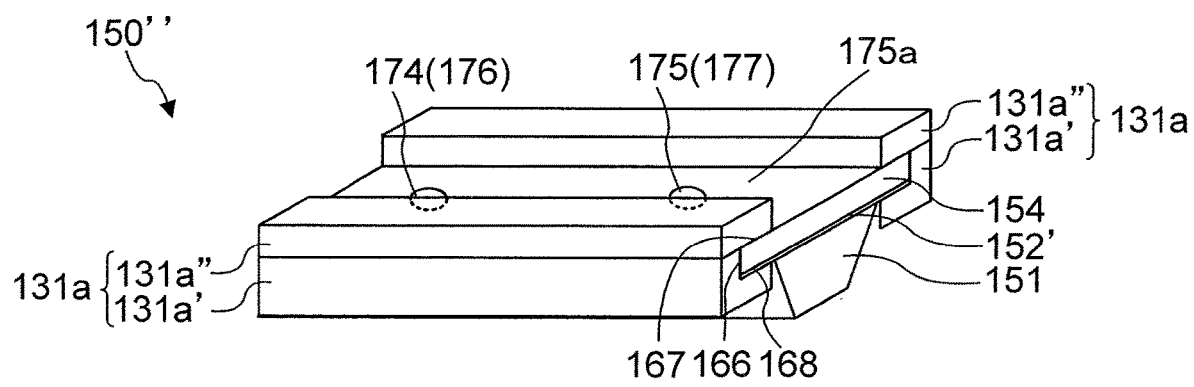
FIG. 6 is a diagram illustrating a configuration of a detection chip according to Variation 2 of Embodiment 1.

FIG. 5A is a diagram illustrating the positional relationship between detection chip 150' of Variation 1 and heat block 131, FIG. 5B is a diagram illustrating the positional relationship between detection chip 150' of Variation 1 and heat block 131a of Variation 1, and FIG. 5C is a diagram illustrating the positional relationship between detection chip 150" of Variation 1 and heat block 131a of Variation 2. FIG. 6 is a diagram illustrating the positional relationship between detection chip 150" of Variation 2 of Embodiment 1 and heat block 131a of Variation 1.

As illustrated in FIG. 5A, metal film 152' of detection chip 150' of Variation 1 is disposed so as to extend to the outer side of film formation surface 162. In addition, base body 154 is disposed so as to cover metal film 152'. In Embodiment 1, bottom surface 168 of base body 154 and metal film 152' are identical in outer diameter. In this case, metal film 152' is heated by heating section 130. More specifically, metal film 152' is heated directly from the side (bottom side) of prism 151 by heat block 131 of heating section 130. Thus, the heating time of the liquid at the reaction site in liquid reservoir section 173 can be shortened. Note that, a through hole may be formed in base body 154, and heating section 130 may heat metal film 152' from the top side. Moreover, metal film 152' may be smaller in outer diameter than bottom surface 168 of base body 154.

As illustrated in FIG. 5B, when detection chip 150' of Variation 1 is heated by heating section 130 having heat block 131a of Variation 1, bottom-side heat block piece 131a' heats base body 154 from metal film 152' and side surface 167. In addition, top-side heat block piece 131a" heats base body 154 from top surface 166.

As illustrated in FIG. 5C, when detection chip 150' of Variation 1 is heated by heating section 130 having heat block 131b of Variation 2, heat block 131b performs heating from metal film 152', bottom surface 164 of prism 151, incident surface 161 of prism 151, and emission surface 163 of prism 151. In this case, heat block 131b has first heat block 131b' on the side of extraction port 177 and second heat block 131b" on the side of injection port 176.

As illustrated in FIG. 6, in detection chip 150" of Variation 2, a transparent conductive film (ITO) or sealing seal 175a made of metal or carbon is disposed so as to cover at least injection port 176. The raw material of sealing film 175a is favorably a highly heat-conductive raw material, and the material having a thermal conductivity equal to or greater than 280 W/(m·K) is favorable. Copper, gold, and aluminum, for example, are favorable as the metal-made sealing seal. In Embodiment 1, sealing seal 175a is disposed on the entirety of top surface 166 of base member 154. In a case where detection chip 150" of Variation 2 is heated by heating unit 130 having heat block 131a of Variation 1, bottom-side heat block piece 131a' heats base body 154 from metal film 152' and side surface 167. In addition, heating section 130 (top-side heat block piece 131a") heats base body 154 by heating sealing seal 175a. Thus, heating the raw material having a high thermal conductivity can shorten the heating time of the liquid at the reaction site in liquid reservoir section 173. Note that, sealing film 175a may be disposed only near injection port 176.

As has been described above, SPFS device 100 according to Embodiment 1 adjusts the reaction of the capturing body and detection target substance, the reaction of the detection target substance and fluorescent material, and the temperature around the fluorescent material from which fluorescence is emitted, to be constant, so that SPFS device 100 can detect the detection target substance with high accuracy and high sensitivity.

Note that, in Embodiment 1, a description has been given of the case where each of heat blocks 131, 131a, and 131b heats base body 154 in a contact state, but heat blocks 131, 131a, and 131b may be configured to heat base body 154 in a non-contact state. In this configuration, the distance between each of heat blocks 131, 131a, and 131b and base body 154 is not limited to any particular distance as long as base body 154 can be heated from the heat from each of heat blocks 131, 131a, and 131b. However, it is favorable that heat blocks 131, 131a, and 131b be positioned as close to base body 154 as possible. In addition, heating section 130 may be configured to heat metal film 152 by induction heating (IH). In this case, an IH coil is disposed in place of each of heat blocks 131, 131a, and 131b.

Embodiment 2

SPFS device 200 according to Embodiment 2 is different from SPFS device 100 according to Embodiment 1 in having reagent storage section 250 and second heating section 230 configured to heat reagent storage section 250. In this respect, the portion different from SPFS device 100 according to Embodiment 1 will be mainly described.

Figure 7:
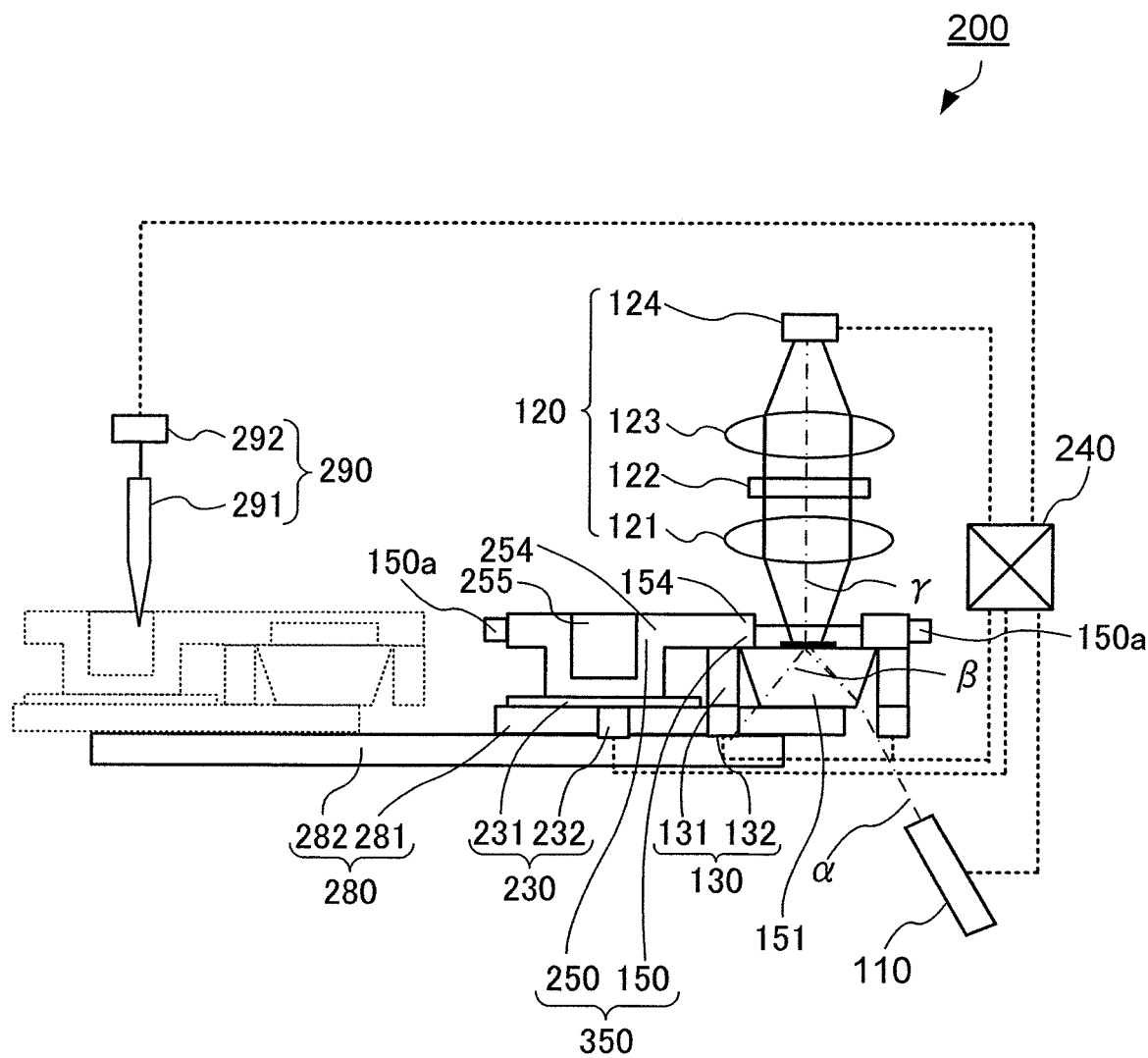
FIG. 7 is a schematic diagram of an SPFS device according to Embodiment 2.

FIG. 7 is a diagram illustrating a configuration of SPFS device 200 according to Embodiment 2. As illustrated in FIG. 7, SPFS device 200 according to Embodiment 2 includes excitation light irradiation section 110, light detection section 120, first heating section 130 (heating section in Embodiment 1), second heating section 230, moving section 280, liquid-feeding section 290, and control section 240. As in Embodiment 1, in detection of a detection target substance, SPFS device 200 is used in a state where detection chip 350 is attached to holder 150a. For this reason, detection chip 350 will be described, first, and each configuration element of SPFS device 200 will be described, thereafter.

Figure 8:
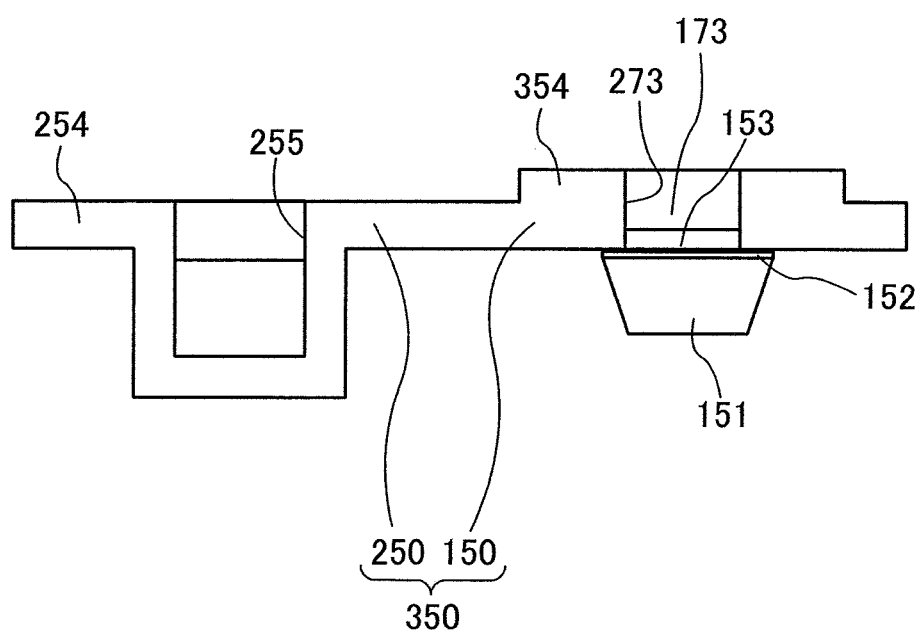
FIG. 8 is a cross-sectional view taken along a long-side direction of a detection chip according to Embodiment 2.

FIG. 8 is a cross-sectional view taken along a long-side direction of detection chip 350 according to Embodiment 2. Note that, hatching of first base body 354 and second base body 254 is omitted in FIG. 8. As illustrated in FIG. 8, detection chip 350 according to Embodiment 2 includes reagent storage section 250 in addition to the configuration elements of detection chip 150 in Embodiment 1.

As illustrated in FIG. 8, detection well 273 is disposed in detection chip 350. Reaction section 153 is disposed at the bottom portion of detection well 273. Reagent storage section 250 includes second base body 254 and a plurality of wells 255. Second base body 254 is a substantially plate-shaped transparent member. Second base body 254 is integrally formed with first base body 354 (base body 154 of Embodiment 1) as a single body.

Well 255 stores a sample and/or a reagent used for the primary reaction and the secondary reaction described above. Well 255 is formed in second base body 254. The shape of well 255 is not limited to a particular shape. Thus, the shape of well 255 is appropriately set in accordance with the amount of a sample or a reagent to be stored therein.

As illustrated in FIG. 7, second heating section 230 indirectly heats, via second base body 254, a liquid stored in reagent storage section 250. Second heating section 230 includes second heat block 231 and second heat source 232. Second heat block 231 heats a liquid to a predetermined temperature in a contact sate or a non-contact state with second base body 254. In Embodiment 2, second heat block 231 is in contact with second base body 254 at least at the time of heating. More specifically, second heat block 231 is disposed at the lower side of well 255. Moreover, for second heat source 232, a heat source identical to first heat source 132 (heat source in Embodiment 1) can be used. The relationship between the temperature of the liquid in detection well 273 and the temperature of the liquid in well 255 is not limited in particular. For example, both of the temperature of the liquid in detection well 273 and the temperature of the liquid in well 255 may be 34 degrees to 40 degrees. Alternatively, the temperature of the liquid in detection well 273 may be 34 degrees to 40 degrees while the temperature of the liquid in well 255 may be 20 degrees to 30 degrees. In the latter case, the temperature of second heat source 232 is 20 degrees to 35 degrees. In addition, when SPFS device 200 is covered by a case, the temperature inside the case can be stabilized.

Moving section 280 includes stage 281 and moving mechanism 282 that moves stage 281. Stage 281 is formed in a plate shape, for example. First heat block 131 (heat block in Embodiment 1) of first heating section 130 and second heat block 231 of second heating section 230 are disposed on stage 281. Detection chip 350 is disposed on stage 281 on which first heat block 131 and second heat block 231 are disposed.

Moving section 280 moves detection chip 350 between the measurement position (position where fluorescence γ generated by emission of excitation light α by excitation light irradiation section 110 is detected by light detection section 120) and the liquid-feeding position (position where a sample or reagent is fed by liquid-feeding section 290).

Liquid-feeding section 290 supplies the sample or reagent stored in reagent storage section 250 to detection well 273 of detection chip 350. Liquid-feeding section 290 includes pipette 291 and pump 292, for example. Suctioning and discharging the sample or reagent is quantitatively performed by driving pump 292.

Control section 240 comprehensively controls excitation light irradiation section 110, light detection section 120, first heating section 130, second heating section 230, moving section 280, and liquid-feeding section 290.

Figure 9:
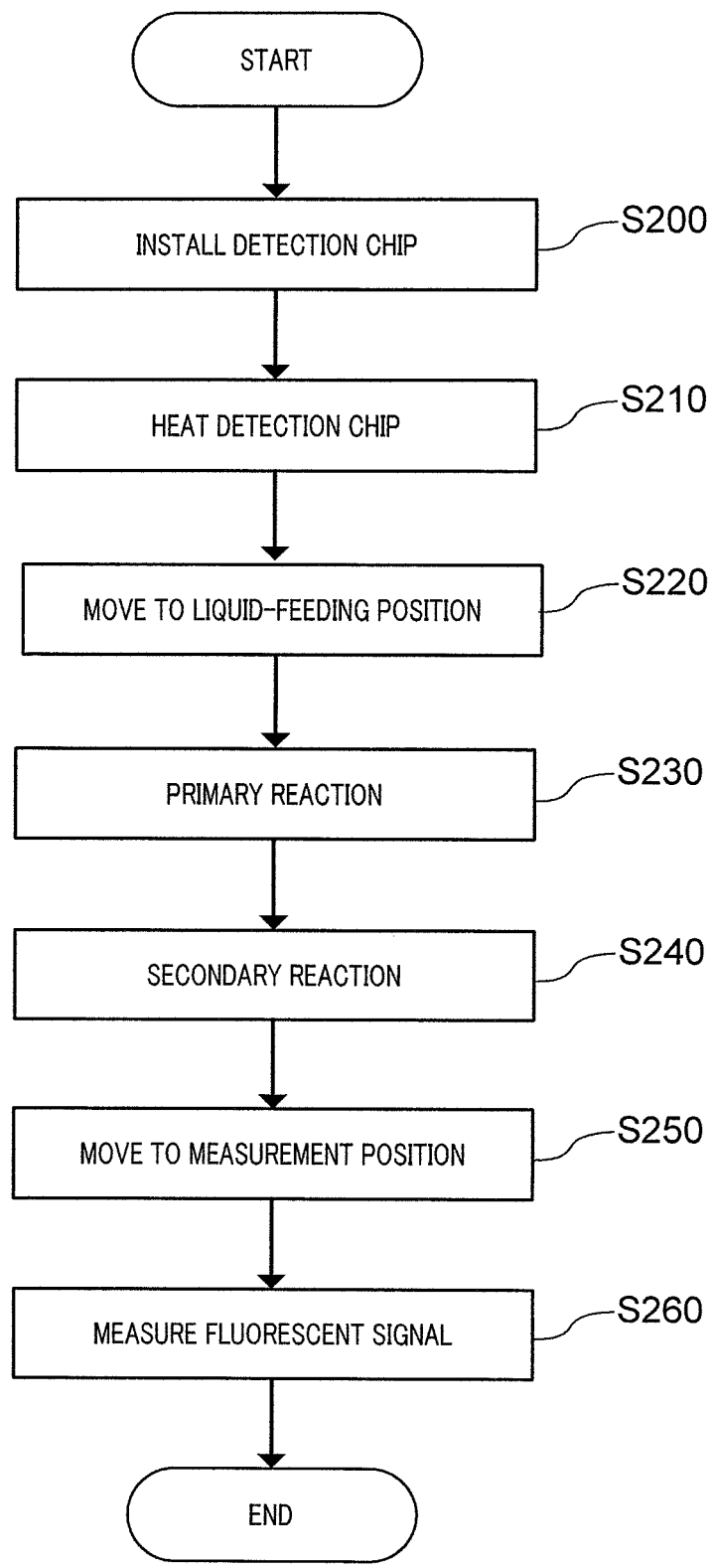
FIG. 9 is a flowchart illustrating an operation procedure of the SPFS device according to Embodiment 2.

Next, a detection operation of SPFS device 200 (detection method according to Embodiment 2 of the present invention) will be described. FIG. 9 is a flowchart illustrating an example of an operation procedure of SPFS device 200.

First, detection chip 350 is installed in holder 150a positioned at an installation positon of detection chip 150 in SPFS device 200 (step S200). At this time, detection chip 350 is installed so as to be in contact with first heat block 131 of first heating section 130 and second heat block 231 of second heating section 230.

Next, control section 240 operates a power supply of first heat source 132 and second heat source 232 to heat first heat block 131 and second heat block 231 (step S210). Thus, the temperatures inside reagent storage section 250 and liquid reservoir section 173 liquid are raised to the same temperature as that of the liquid at the reaction site. In Embodiment 2, the temperature of the liquid at the reaction site is 37 degrees and is the optimum temperature for the primary reaction and the secondary reaction.

Next, control section 240 operates moving mechanism 282 and moves detection chip 350 to the liquid-feeding position (step S220).

Subsequently, control section 240 operates liquid-feeding section 290 and introduces the sample in reagent storage section 250 into detection well 273 of detection chip 350 (step S230). In detection well 273, in order for the capturing body (primary antibody) fixed to reaction section 153 to surely capture the detection target substance (antigen-antibody reaction), pump 292 is driven to agitate the sample in detection well 273. At this time, since the temperatures inside reagent storage section 250 and liquid reservoir section 173 are adjusted to the same temperature as the analysis temperature, the temperature of the liquid does not go down, and the reaction proceeds promptly. The detection target substance contained in the sample is then surely captured by the capturing body (primary antibody). Subsequently, the sample inside detection well 273 is removed, and the inside of detection well 273 is cleaned using a cleaning liquid.

Subsequently, control section 240 operates liquid-feeding section 290 and introduces the reagent (labeling solution) containing the secondary antibody labeled by a fluorescent material into detection well 273 of detection chip 350 (step S240). In this case as well, since the reagent fed to detection well 273 is previously heated to the temperature at the time of analysis when the secondary antibody and detection target substance react with each other, the temperature does not go down. The secondary antibody labeled by the fluorescent material contained in the reagent is surely bonded to the detection target substance. Thus, the detection target substance is labeled by the fluorescent material. Subsequently, the labeling solution inside detection well 273 is removed, and the channel is cleaned using a cleaning liquid.

Next, control section 240 operates moving mechanism 282 and moves detection chip 350 from the liquid-feeding position to the measurement position (step S250). Detection chip 350 is irradiated with excitation light α from the light source in such a way that excitation light α is incident on metal film 152 at a specific incident angle (step S260).

The presence or amount of the detection target substance of the sample can be detected by the procedure mentioned above.

As has been described, SPFS device 200 according to Embodiment 2 can further detect the detection target substance with high accuracy and high sensitivity as compared with SPFS device 100 according to Embodiment 1 because reagent storage section 250 is also heated.

Note that, in Embodiment 2, a description has been given of the case where heating is performed while first heat block 131 and second heat block 231 are in contact with base body 154 and second base body 254, respectively, but heating may be performed while first heat block 131 and second heat block 231 are not in contact with base body 154 and second base body 254. In this case, the distances between first heat block 131 and base body 154, and second heat block 231 and second base body 254 are not limited in particular as long as base body 154 and second base body 254 can be heated by the heat from first heat block 131 and second heat block 231, respectively, but the shorter the better.

Moreover, in Embodiment 2, reagent storage section 250 is heated by second heating section 230, but may not be heated. In other words, in Embodiment 2, only detection well 273 may be heated. In this case, the proportion of detection chip 350 that is occupied by detection well 273 is so small that the reagent injected into detection well 273 increases in temperature right after the injection. Moreover, since second heating section 230 is not necessary, designing can be implemented easily as compared with Embodiment 2 in which detection well 273 and reagent storage section 250 are heated. Moreover, the temperature of detection well 273 goes up fast as compared with detection chip 350 according to Embodiment 2.

Furthermore, in Embodiment 2, first and second heat blocks 131 and 231 are controlled by first and second heat sources 132 and 232, respectively, but may be controlled by a single heating section. Thus, first and second heat blocks 131 and 231 can be controlled simply (Variation of Detection Chip)

Figure 10:
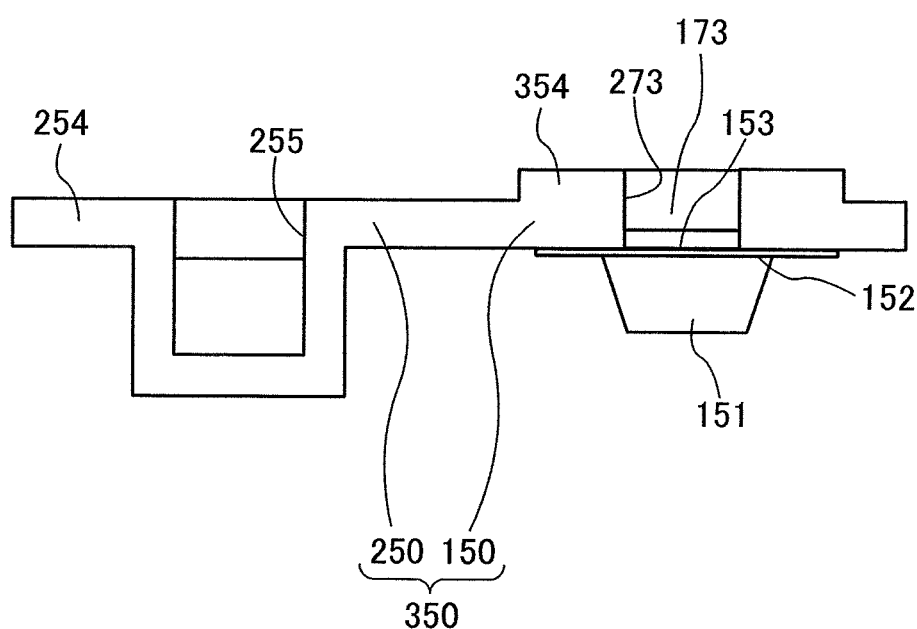
FIG. 10 is a cross-sectional view taken along a long-side direction of a detection chip according to a variation of Embodiment 2.

FIG. 10 is a cross-sectional view taken along a long-side direction of detection chip 350 of a variation of Embodiment 2. As illustrated in FIG. 10, metal film 152 of detection chip 350 of the variation of Embodiment 2 is disposed so as to extend to the outer side of film formation surface 162. In this case, heat block 131 of heating section 130 can directly heat metal film 152, so that the heating time of the liquid at the reaction site in liquid reservoir section 173 can be shortened.

Note that, first and second heating sections 130 and 230 illustrated in FIG. 7 may be configured to heat metal film 152 using induction heating (IH). In this case, an IH coil is disposed instead of each of heat blocks 131 and 231.

Although a description has been given of the SPFS devices in Embodiments 1 and 2, the detection device according to the present invention is not limited to an SPFS device. For example, the detection device according to the present invention may be an SPR device. In this case, the SPR device includes a light detection section configured to detect the excitation light reflected by a metal thin film and emitted from an emission surface.

This application is entitled to and claims the benefit of Japanese Patent Application No. 2013-226952 filed on Oct. 31, 2013, the disclosure of which including the specification, and drawings is incorporated herein by reference in its entirety.

INDUSTRIAL APPLICABILITY

The detection device, and detection method using surface plasmon resonance, and the detection chip used in the device and method, according to the present invention, enable highly reliable measurement of a detection target substance, so that they are useful in laboratory tests or the like, for example.

REFERENCE SIGNS LIST 100, 200 SPFS device
110 Excitation light irradiation section
120 Light detection section
121 First lens
122 Filter
123 Second lens
124 Light sensor
130 Heating section (first heating section)
131 Heat block (first heat block)
132 Heat source (first heat source)
133 Recess section
140, 240 Control section
150, 350 Detection chip (detection section)
150a Holder
151 Prism
152 Metal film
153 Reaction section
154, 354 Base body (first base body)
161 Incident surface of prism
162 Film formation surface of prism
163 Emission surface of prism 164 Bottom surface of prism
166 Top surface of base body
167 Side surface of base body
168 Bottom surface of base body
171 Channel groove
172 Channel
173 Liquid reservoir section
174 First through hole
175 Second through hole
175a Sealing seal
176 Injection port
177 Extraction port
230 Second heating section
231 Second heat block
232 Second heat source
250 Reagent storage section
254 Second base body
255 Well
273 Detection well
280 Moving section
281 Stage
282 Moving mechanism
290 Liquid-feeding section
291 Pipette
292 Pump

The invention claimed is:

1. A detection device that detects the presence or amount of a detection target substance contained in a sample, using surface plasmon resonance, the detection device comprising:
  a holder that holds a detection chip,
  the detection chip comprising:
    a prism including an incident surface and a film formation surface,
    a metal film disposed on the film formation surface;
    a capturing body disposed on the metal film; and
    a base body disposed to be flush with a surface of the metal film, the surface being where the capturing body is disposed, and the base body being configured to form, together with the metal film, a liquid reservoir that reserves a liquid,
  a light source that emits excitation light toward the incident surface; and
  a heating section that heats at least any one of the base body, the prism, and the metal film, in a contact state or a non-contact state, wherein
  the heating section is disposed while avoiding a light path of the excitation light from the light source to the incident surface,
  the detection chip further comprises a reagent storage that stores a sample or reagent to be supplied to the liquid reservoir, the reagent storage not being communicated with the liquid reservoir, and
  the heating section further heats the reagent storage in a non-contact state.

2. The detection device according to claim 1, wherein the heating section heats at least any one of a top surface, a side surface, and a bottom surface of the base body.

3. The detection device according to claim 1, wherein the heating section heats a bottom surface of the prism, the bottom surface being opposite to the film formation surface.

4. The detection device according to claim 1, wherein the heating section heats a bottom surface of the base body, an incident surface of the prism, a bottom surface of the prism, and an emission surface of the prism, the bottom surface of the prism being opposite to the film formation surface, and the emission surface being configured to emit excitation light reflected by the film formation surface.

5. The detection device according to claim 1, wherein the heating section does not heat the reagent storage.

6. The detection device according to claim 1, wherein the heating section heats the metal film by induction heating.

7. The detection device according to claim 1, wherein the metal film is disposed so as to extend to an outer side of the film formation surface, and the heating section heats the metal film.

8. The detection device according to claim 1, wherein the base body includes an injection port for injecting the sample into the liquid reservoir, wherein
  the detection chip further comprises a carbon-made sealing seal that seals the injection port, and
  the heating section and the sealing seal being in such proximity to each other that the heating section heats the base body by heating the sealing seal.

* * * * *